United States Patent [19]

Sakamoto et al.

[11] Patent Number: 4,725,547

[45] Date of Patent: * Feb. 16, 1988

[54] METHOD FOR PURIFICATION OF RABIC VIRUS

[75] Inventors: Kuniaki Sakamoto; Kunio Ohkuma, both of Kumamoto; Tetsuo Kawahara, Ohzu; Mitsuo Sakoh, Kumamoto, all of Japan

[73] Assignee: Juridical Foundation The Chemo-Sero-Therapeutic Research Institute, Kumamoto, Japan

[*] Notice: The portion of the term of this patent subsequent to May 7, 2002 has been disclaimed.

[21] Appl. No.: 764,132

[22] Filed: Aug. 9, 1985

[30] Foreign Application Priority Data

Aug. 10, 1984 [JP] Japan ................... 59-168226

[51] Int. Cl.[4] .................. C12N 7/02; C12N 7/00; A61K 39/12
[52] U.S. Cl. .................... 435/239; 435/235; 424/89
[58] Field of Search ............. 435/235, 803, 239; 424/89; 210/927; 530/412, 413

[56] References Cited

U.S. PATENT DOCUMENTS

| | | | |
|---|---|---|---|
| 3,842,062 | 10/1974 | Eastman | 530/411 |
| 3,920,625 | 11/1975 | Andersson et al. | 530/382 |
| 3,973,000 | 8/1976 | Lavender | 424/89 |
| 4,115,195 | 9/1978 | Barth et al. | 424/89 X |
| 4,138,287 | 2/1979 | Andersson et al. | 435/239 |
| 4,160,019 | 7/1979 | Bjorklund | 436/520 |
| 4,168,300 | 9/1979 | Andersson et al. | 436/514 |
| 4,181,713 | 1/1980 | McAleer et al. | 424/86 |
| 4,255,520 | 3/1981 | Schell | 435/239 |
| 4,320,115 | 3/1982 | Bijlenga | 424/89 |
| 4,434,093 | 2/1984 | Zolton et al. | 252/626 |
| 4,515,714 | 5/1985 | Kawahara et al. | 530/380 |

OTHER PUBLICATIONS

Nilsson et al, "Immobilization of Enzymes and Affinity Ligands to Various Hydroxyl Group Carrying Supports Using Highly Reactive Sulfonyl Chlorides", Biochem. and Biophys. Research Comm., 102, (1):449–457, (1981).

Einarsson et al, "A Two-Step Procedure for the Purification of Hepatitis B Surface Antigen (HBsAg)", Vox Sang: 41:91–97, (1981).

Einarsson et al, "Purification of Hepatitis B Surface Antigen by Affinity Chromatography", Vox Sang, 35:224–233, (1978).

Wilchek et al, "Structure of a Soluble Super-Active Insulin is Revealed by the Nature of the Complex Between Cyanogen Bromide Activated Sepharose and Amines", Proc. Nat. Acad. Sci. USA, 72,(3):1055–1058, (1975).

Primary Examiner—Esther M. Kepplinger
Assistant Examiner—Shawn P. Foley
Attorney, Agent, or Firm—Fleit, Jacobson, Cohn & Price

[57] ABSTRACT

Disclosed is a method for the purification of rabic virus, which comprises subjecting a solution containing the rabic virus to column chromatography using, as a gel for chromatography, a sulfuric acid ester of cellulose or a crosslinked polysaccharide. The method can provide highly purified rabic virus which is useful for obtaining an effective vaccine against rabies.

6 Claims, No Drawings

METHOD FOR PURIFICATION OF RABIC VIRUS

BACKGROUND OF THE INVENTION

The present invention relates to a method for the purification of rabic virus, and particularly to such method for obtaining effective vaccines against rabies.

Rabies is a disease occuring almost all over the world, particularly in Asian and African countries. This disease is caused by rabic virus, which is known to be a bullet-shaped RNA virus belonging to Rhabdoviridae measuring about 180 nm in length and about 80 nm in diameter. The virus is infective to mammalian animals. Thus, rabies is mediated even through wild animals such as bats, foxes, weasels etc. as well as dogs. Affliction with rabies occurs upon the invasion of rabic virus into the central nervous system through peripheral nerves and is tranmitted from an animal infected with the virus by biting or licking. The mortality rate in human patients approaches almost 100 percent.

The only possible way for preventing and curing such horrible disease is a vaccination, in which a highly purified vaccine is desired to be used.

A typical conventional method for the production of a rabies vaccine, particularly for animals, includes the step of preparing a rabic virus-containing material by propagating rabies virus infected into the brains of mice or any other appropriate animals and harvesting the propagated virus from the brains and the step of refining or purifying the harvested material by means of centrifugation and/or chemical treatments with such agent as sodium carboxymethyl cellulose, followed by an inactivation treatment. More recently, particularly in the case of production of rabies vaccine for human beings, tissue-culture types of rabies vaccines have been developed in which there is used such cell as cultured chick embryo cell. This type of vaccine is more effective and safe because there are contained the less contaminants as would orginate from the brain substances. A typical dried inactivated tissue culture rabies vaccine of such type is prepared as follows:

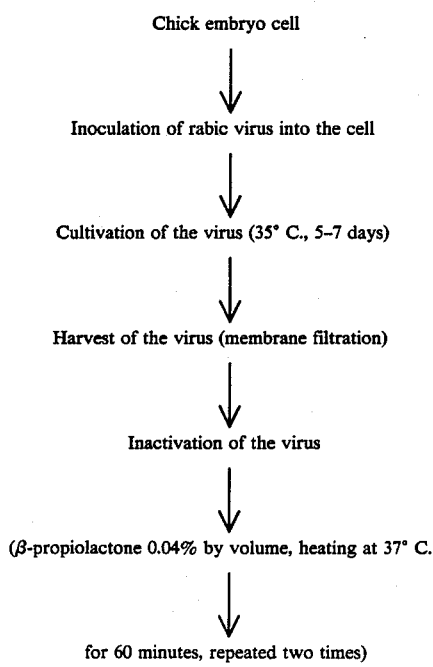

Chick embryo cell
↓
Inoculation of rabic virus into the cell
↓
Cultivation of the virus (35° C., 5-7 days)
↓
Harvest of the virus (membrane filtration)
↓
Inactivation of the virus
↓
(β-propiolactone 0.04% by volume, heating at 37° C.
↓
for 60 minutes, repeated two times)
↓
Concentrating by ultrafiltration
↓
Ultra-high-speed centrifugation
↓
Precipitate  Supernatant
↓
Treatment with sodium chloride-containing
↓
buffer solution (M/100, pH 7.1)
↓
Conditioning
↓
Final bulk
↓
Freeze drying However, the conventional methods for preparing rabies vaccine, including the one as illustrated by the above flow diagram, require sophisticated and costly techniques, such as ultrafiltration and ultrahigh-speed centrifugation, to purify rabic virus and only produce vaccines of low purities.

SUMMARY OF THE INVENTION

It is therefore a primary object of the present invention to provide a method by which rabic virus can be purified in a simple and unexpensive manner to produce a rabies vaccine of high purity.

Other objects and features of the present invention will be apparent from the following description.

The present invention is based on the discovery that a sulfuric acid ester of cellulose or a crosslinked polysaccharide has a specific affinity with rabic virus, and is effective for isolation and purification of the virus from a material containing the same. Thus, according to the present invention, there is provided a method for the purification of rabic virus which comprises subjecting a solution containing the rabic virus to column chromatography using, as a gel for chromatography, a sulfuric acid ester of a crosslinked polysaccharide or cellulose.

The sulfuric acid ester of cellulose to be used in the present invention includes a sulfuric acid ester of crystalline cellulose or cellulose having crystalline area and non-crystalline area. These starting celluloses are commercially available, for example, as Abicel (manufactured by Asahi Kasei in Japan), Cellulofine GC-15, GH-25, GC-100, or GC-200 (manufactured by Chisso Corp. in Japan).

The sulfuric acid ester of a crosslinked polysaccharide to be used in the present invention includes a sulfuric acid ester of polysaccharides, such as dextran, cellulose, agarose, which is crosslinked with a crosslinked agent, such as epichlorohydrin, dichlorohydrin dibromohydrin, ethylene glycol bisepoxypropyl ether. The crosslinked polycaccharides are commercially available, for example, as crosslinked dextran such as Sephadex G-10, G-25, G-50, and G-100 (manufactured by Pharmacia in Sweden), crosslinked agaroses such as Sepharose Cl-2B, Cl-4B, and Cl-6B (manufactured by Pharmacia in Sweden), and crosslinked celluloses such as Cellulofine GCL-25, GCL-90 (manufactured by Chisso Corp. in Japan).

The sulfation of such crosslinked polysaccharide or cellulose can be carried out by a conventional method. However, the gel for chromatography to be used in the present invention is characterized in that it is prepared by directly sulfating cellulose or a crosslinked polysaccharide, which are water-insoluble, with a sulfating agent such as chlorosulfonic acid or anhydrous sulfuric acid in an organic solvent (e.g. pyridine). Thus, the resultant gel is water-insoluble and highly stable. Further, such gel of the sulfuric acid ester of cellulose or a crosslinked polysaccharide exhibits an extremely high adsorbing activity since it is fully sulfated, even at the inner regions thereof. The use of the gel is also advantageous from an economical standpoint, because it can be easily prepared at a low cost. The degree of sulfation (content of the sulfonyl group) of crosslinked polysaccharide is usually in the range of 0.1 to 40%, preferably 10 to 40%, based on the weight of the crosslinked polysaccharide, and the degree of sulfation of cellulose is usually in the range of 0.1 to 5.0%, based on the cellulose.

The procedure of purification of rabic virus by column chromatography using the sulfuric acid ester of a crosslinked polysaccharide or cellulose is carried out in a similar manner to that in conventional column chromatography. For instance, the method is carried out in the following manner: first, a sulfuric ester of a crosslinked polysaccharide or cellulose (preferably, in the form of spherical particles) is packed within a column, which is equilibrated with a suitable buffer solution, preferably having an ionic strength of about 0.001 to 2.0, for example, 0.01 M phosphate buffered saline solution containing 0.14 M NaCl (pH 7.0–8.0). After the equilibration, a rabic virus-containing solution to be treated is passed through the column in order to adsorb such virus onto the gel, followed by washing with the same buffer solution as used for the the above equilibration. Thereafter, the adsorbed influenza virus is eluted from the column by passing through the column a suitable buffer solution having an ionic strength larger than that of the buffer solution used for the equilibration or the washing, for example, 1.0 M or 1.5 M sodium chloride-containing phosphate buffer solution (pH 6–9) to give desired highly purified rabic virus.

The method of the present invention can be applied to any solution containing rabic virus and can be conducted at any stage in the purification of rabic virus. Thus, the method can be applied to a solution containing rabic virus before being subjected to an inactivation treatment as well as an inactivated rabic virus-containing solution. For example, a solution just harvested from the cultured chick embryo cell as mentioned above can undergo the method of the present invention in order to purify or isolate rabic virus contained therein. An inactivatied rabic virus-containing solution, such as one obtained by the inactivation with β-propiolactone as mentioned or with ultraviolet rays, can also be subjected to the method of the invention for purifying the virus. The present invention can be of course applied to a rabic virus-containing solution produced by any other process, for example, those obtained by propagating rabic virus infected into the brains of mice or any other animals. The method of the present invention may also be applied to a solution containing rabic virus proteins which would be expressed by means of genetic engineering.

According to the purification method of the present invention rabic virus can be purified to a high degree, with the least contamination with proteins, lipids and other substances resulting from the cell used and/or the culturing medium. This is probably due to the fact that the sulfonyl group bonds directly to the crosslinked polysaccharide or cellulose in the sulfuric acid ester of a crosslinked polysaccharide or cellulose and hence it has a high content of sulfonyl group and shows excellent specific adsorbability to rabic virus. The purification method of the present invention can be easily done with simple operation without need for expensive equipment give the desired purified rabic virus on an industrial scale with lower cost. If desired, the method of the present invention can be combined with conventional separation techniques (e.g. ultracentrifugation) so as to obtain rabic virus as highly as possible.

The present invention will now be illustrated by the following Preparations (preparations of gels for chromato-graphy) and Examples, but should not be construed to be limited thereto.

Preparation 1

To pyridine (600 ml) is added dropwise chlorosulfonic acid (117 g) at below 0° C. After the addition, the mixture is heated to 65°–70° C. To the mixture is added crystalline cellulose gel (Cellulofine GC-15, manufactured by Chisso Corp.)(80 g), and the mixture is stirred at 65°–70° C. for 3 hours. After the completion of the reaction, the mixture is cooled and neutralized with 10% aqueous sodium hydroxide. The gel thus obtained is separated by filtration and washed well with 0.01 M phosphate buffer-aqueous sodium chloride mixture to give a cellulose sulfate gel.

Preparation 2

To pyridine (600 ml) is added dropwise chlorosulfonic acid (117 g) at below 0° C. After the addition, the mixture is heated to 65°–70° C. To the mixture is added crystalline cellulose (Abicel for chromatography, manufactured by Asahi Kasei)(80 g), and the mixture is stirred at 65°–70° C. for 4 hours. After the completion of the reaction, the reaction mixture is cooled and then neutralized with 10% aqueous sodium hydroxide. The gel thus obtained is separated by filtration and washed well with 0.01 M phosphate buffer-aqueous sodium chloride mixture to give a cellulose sulfate gel.

Preparation 3

To pyridine (200 ml) is added dropwise chlorosulfonic acid (11 ml) at below 0° C. After the addition, the mixture is heated to 65°–70° C. To the mixture is added epichlorohydrin-crosslinked dextran (Sephadex G-50, manufactured by Pharmacia)(7.5 g), and the mixture is stirred at 65°–70° C. for 4 hours. After the reaction, the reaction mixture is cooled and then neutralized with aqueous sodium hydroxide. The gel thus obtained is separated by filtration and washed well with 0.01 M phosphate-buffered saline solution to give a crosslinked dextran sulfate.

EXAMPLE 1

The cellulose sulfate gel obtained in the manner as described in Preparation 1 is packed within a column (25 mm$\phi$×400 mm), followed by the passage of 1,400 ml of distilled water through the column. The packed column is equilibrated with 0.01 M phosphate-buffered saline solution containing 0.14 M sodium chloride. Then, through the column is passed, at a rate of 500 ml/minute, 2,900 ml of an inactivated rabic virus-containing solution obtained by using chick embryo cell followed by an inactivation treatment, as described in the above. After the passage of the virus containing solution, the column is fully washed with 0.01 M phosphate buffer solution containing 0.14 M sodium chloride. Then, the adsorbed material is eluted with 500 ml of 0.01 M phosphate buffer solution containing 1.0 M sodium chloride (specific conductivity 87.6 mS/cm, pH 7.3) at a rate of 1 ml/minute. The starting solution and the eluate are determined with respect to the respective virus contents in terms of HA (Hemagglutinin) titer. Determination is also made with respect to the amounts of the contaminant proteins resulted from the cell used, in comparison with the conventional method in which the inactivated virus-containing solution is purified by the ultrafiltration and the ultrahigh-speed centrifugation. The results are shown in Table 1, which demonstrates that the viruscontained in the starting solution is sufficiently recovered by the method of the invention, and the degree of purification by the method of the present invention, in terms of the amount of the contaminant proteins, is approximately two times as high as that by the conventional method.

TABLE 1

| Virus Content(HA titer) | | Contaminant Proteins | |
|---|---|---|---|
| Starting Solution | Eluate | Conventional Method | Present Invention |
| 185,600 | 335,360 | 0.027 mg/ml | 0.014 mg/ml |

EXAMPLE 2

Using the cellulose gel obtained in Preparation 2, a procedure is conducted similar to Example 1 except that 4,200 ml of the inactivated rabic virus-containing solution is passed through the column and the adsorbed material is eluted with 0.01 M phosphate buffer solution containing 1.5 M NaCl (specific conductivity 120 mS/cm, pH 7.2). The results are summarized in Table 2.

TABLE 2

| Virus Content(HA titer) | | Contaminant Proteins | |
|---|---|---|---|
| Starting Solution | Eluate | Conventional Method | Present Invention |
| 134,000 | 204,800 | 0.020 mg/ml | 0.014 mg/ml |

EXAMPLE 3

Using the crosslinked dextran sulfate gel, a purification procedure is conducted in a similar manner to that in Example 1, except that a solution just harvested from the cultured chick embryo cell (a solution prior to the inactivation) is used in an amount of 3,000 ml. The virus content and the amounts of the contaminant proteins are determined in the same manners as in Example 1, with the results shown in Table 3.

TABLE 3

| Virus Content(HA titer) | | Contaminant Protein | |
|---|---|---|---|
| Starting Solution | Eluate | Conventional Method | Present Invention |
| 105,600 | 176,500 | 0.028 mg/ml | 0.015 mg/ml |

What is claimed is:

1. A method for the purification of rabic virus, which comprises subjecting a solution containing the rabic virus to column chromatography using, as a gel for chromatography, a sulfuric acid ester of cellulose or a crosslinked polysaccharide, said sulfuric acid ester being prepared by treating a gel of cellulose or crosslinked polysaccharide with a sulfating agent in an organic solvent.

2. The method as claimed in claim 1, wherein the rabic virus-containing solution is one obtained by propagating rabic virus using a cell culture of chick embryo followed by an inactivation of the virus.

3. The method as claimed in claim 1, wherein the rabic virus-containing solution is one harvested from a culture medium using a cell culture of chick embryo.

4. The method as claimed in claim 1, wherein the rabic virus-containing solution is one obtained by propagating rabies virus infected into the brains of mice.

5. The method as claimed in of claim 1, wherein the sulfuric acid ester of a crosslinked polysaccharide is selected from the group consisting of a crosslinked cellulose sulfate, a crosslinked agarose sulfate and a crosslinked dextran sulfate.

6. The method as claimed in of claim 1, wherein the sulfuric acid ester of cellulose is a sulfuric acid ester of crystalline cellulose or a cellulose having a crystalline area and non-crystalline area.

* * * * *